United States Patent [19]

Ratcliffe

[11] Patent Number: 5,039,710
[45] Date of Patent: Aug. 13, 1991

[54] HOMOCYCLIC DERIVATIVES

[75] Inventor: Arnold H. Ratcliffe, Poynton, United Kingdom

[73] Assignee: Imperial Chemical Industries PLC, London, England

[21] Appl. No.: 584,490

[22] Filed: Sep. 17, 1990

Related U.S. Application Data

[60] Continuation of Ser. No. 269,318, Nov. 10, 1988, abandoned, which is a division of Ser. No. 54,897, May 28, 1987, Pat. No. 4,803,201, which is a continuation of Ser. No. 895,582, Aug. 13, 1986, abandoned, which is a continuation of Ser. No. 515,529, Jul. 20, 1983, abandoned.

[30] Foreign Application Priority Data

Nov. 10, 1982 [GB] United Kingdom ................ 8232084

[51] Int. Cl.$^5$ .......................................... A61K 31/045
[52] U.S. Cl. ................................... 514/729; 514/462; 514/511; 514/693; 549/228; 558/270; 558/275; 568/445; 568/817
[58] Field of Search ................ 568/817, 445; 558/270, 558/275; 549/228; 514/729, 511, 693, 462

[56] References Cited

U.S. PATENT DOCUMENTS 3,761,512  9/1973  Borrow ............................... 568/817

FOREIGN PATENT DOCUMENTS 62-155232  7/1987  Japan .
1331520  9/1973  United Kingdom .

OTHER PUBLICATIONS

Ipsen, J. Org. Chem., 47, pp. 3278–3282 (1982).
Roche, "Design of Biopharmaceutical Properties Through Prodrugs and Analogs," pp. 27–46 & 281–315 (1977).

*Primary Examiner*—Michael L. Shippen
*Attorney, Agent, or Firm*—Cushman, Darby & Cushman

[57] ABSTRACT

Aphidicolane derivatives of the formula:

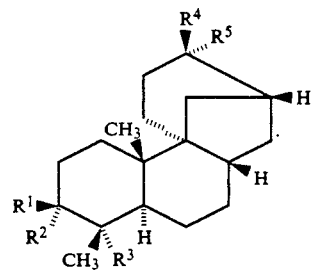

wherein $R^1$ stands for hydrogen or a hydroxy radical, $R^2$ stands for a hydroxy or methyl radical, or the group $CR^1R^2$ stands for a keto group; $R^3$ stands for a formyl or hydroxymethyl radical, or for the group —$CH_2O.CO.OR^6$, wherein $R^6$ stands for a defined radical or $R^2$ and $R^3$ are joined together to form the group —$O.CO.OCH_2$—; $R^4$ stands for a hydroxy radical; $R^5$ stands for a formyl radical, a hydroxyalkyl radical —$(CH_2)_{1-3}OH$, a radical —$CHR^7OH$, wherein $R^7$ stands for a defined radical, or $R^5$ stands for an azidomethyl or pyrrolidinylcarbonyloxymethyl radical, or for the group —$CH_2O.CO.OR^8$, wherein $R^8$ stands for a defined radical, or $R^5$ stands for the group —$CH_2O.CO.(CH_2)_m.CR^{11}R^{12}.(CH_2)_n.NR^9R^{10}$, wherein m, n, $R^9$, $R^{10}$, $R^{11}$ and $R^{12}$ have defined values, or $R^5$ stands for the group —$CH_2O.SO_2.R^{13}$, wherein $R^{13}$ stands for a defined radical; or $R^4$ and $R^5$ are joined together to form the group —$O.CH_2$— or —$O.CO.OCH_2$—; and, where appropriate, pharmaceutically-acceptable salts thereof. Processes for the preparation of said aphidicolane derivatives. Pharmaceutical compositions comprising one of the compounds and a pharmaceutical diluent or carrier. The compounds exhibit inhibitory activity against DNA-containing viruses and they inhibit the growth of some tumors.

7 Claims, No Drawings

HOMOCYCLIC DERIVATIVES

This is a continuation of application Ser. No. 07/269,318, filed on Nov. 10, 1988, which was abandoned upon the filing hereof, which is itself a Rule 60 divisional of 054,897 filed May 28, 1987, now U.S. Pat. No 4,803,201; which is a Rule 60 continuation of 895,582, filed Aug. 13, 1986 now abandoned; which is a Rule 62 continuation of 515,529 filed Jul. 20, 1983, now abandoned.

This invention relates to homocyclic derivatives, and more particularly it relates to aphidicolin derivatives which possess inhibitory activity against DNA-containing viruses and which inhibit the growth of certain tumours.

Aphidicolin is a known compound which has the following structure:

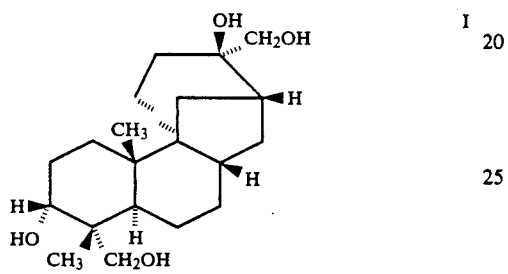

I

It is produced by the fermentation of *Cephalosporium aphidicola*, *Nigrospora sphaerica* and *Harziella entomophilla*, and it is known from United Kingdom patent specification No. 1,331,520 to be a mitotic suppressant and to possess inhibitory activity against DNA-containing viruses, for example *Herpes simplex* and *Vaccinia* viruses. Also, aphidicolin has been tested against certain tumours in experimental animals, and encouraging results have been obtained.

According to the invention there are provided compounds of the formula:

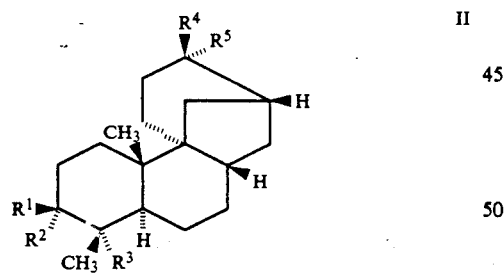

II wherein:

$R^1$ stands for hydrogen or a hydroxy radical;

$R^2$ stands for a hydroxy or methyl radical; or the group $CR^1R^2$ stands for a keto group;

$R^3$ stands for a formyl or hydroxymethyl radical, or a group of the formula $-CH_2O.CO.OR^6$, wherein $R^6$ stands for a phenyl radical which may optionally be substituted by an amino radical, an alkylamino radical of not more than 6 carbon atoms, or dialkylamino radical of not more than 12 carbon atoms, or a carboxy or hydroxysulphonyl radical, or $R^6$ stands for a phenylalkyl radical of not more than 9 carbon atoms which may optionally bear an amino radical, an alkylamino radical of not more than 6 carbon atoms, a dialkylamino radical of not more than 12 carbon atoms, or a carboxy or hydroxysulphonyl radical, on the phenyl moiety;

or $R^2$ and $R^3$ are joined together to form the group of the formula $-O.CO.OCH_2-$;

$R^4$ stands for a hydroxy radical;

$R^5$ stands for a formyl radical, a hydroxyalkyl radical of the formula $-(CH_2)_{1-3}OH$, a radical of the formula $-CHR^7OH$, wherein $R^7$ stands for an alkyl radical of not more than 3 carbon atoms, a phenyl radical which may optionally be substituted by an amino radical, an alkylamino radical of not more than 6 carbon atoms, a dialkylamino radical of not more than 12 carbon atoms, or a carboxy or hydroxysulphonyl radical, or $R^5$ stands for an azidomethyl or pyrrolidinylcarbonyloxymethyl radical, or for a group of the formula $-CH_2O.CO.OR^8$, wherein $R^8$ stands for a phenyl radical which may optionally be substituted by an amino radical, an alkylamino radical of not more than 6 carbon atoms, a dialkylamino radical of not more than 12 carbon atoms, or a carboxy or hydroxysulphonyl radical, or a phenylalkyl radical of not more than 9 carbon atoms which may optionally bear an amino radical, an alkylamino radical of not more than 6 carbon atoms, a dialkylamino radical of not more than 12 carbon atoms, or a carboxy or hydroxysulphonyl radical, on the phenyl moiety, or $R^8$ stands for a piperidinyl radical or an N-substituted piperidinyl radical of the formula:

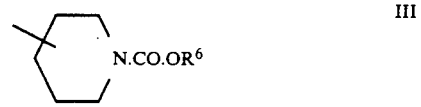

III wherein $R^6$ has the meaning stated above, or $R^5$ stands for a group of the formula:

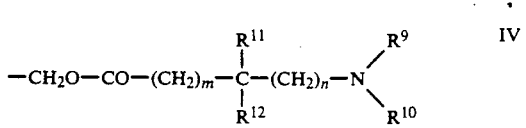

IV wherein m and n, which may be the same or different, stand for 0 to 4, provided that m and n together do not total more than 4, $R^9$ stands for hydrogen, an alkyl radical of not more than 6 carbon atoms, an aryl radical of not more than 10 carbon atoms, a phenylalkyl radical of not more than 9 carbon atoms, an alkoxycarbonyl radical of not more than 6 carbon atoms, or a $R^6O.CO$ radical wherein $R^6$ has the meaning stated above, and $R^{10}$ stands for hydrogen or an alkyl radical of not more than 6 carbon atoms, or $R^9$ and $R^{10}$ are joined to form, together with the adjacent nitrogen atom, a saturated nitrogen-containing heterocyclic radical, and $R^{11}$ stands for hydrogen, an alkyl radical of not more than 4 carbon atoms, a phenyl radical which may optionally be substituted by an alkyl or alkoxy radical of not more than 4 carbon atoms, or $R^{11}$ stands for a phenylalkyl radical of not more than 9 carbon atoms which may optionally be substituted on the phenyl moiety by an alkyl or alkoxy radical of not more than 4 carbon atoms, and $R^{12}$ stands for hydrogen or an alkyl radical of not more than 4 carbon atoms, or $R^5$ stands for a group of the formula $-CH_2O.SO_2.R^{13}$, wherein $R^{13}$ stands for an alkyl radical of not more than 3 carbon atoms, or a phenyl, tolyl or carboxyphenyl radical, or a naphthyl radical which may optionally be substituted by a dialkylamino radical of not more than 6 carbon atoms; or $R^4$ and $R^5$ are joined together to form the group —O.CH$_2$— or —O.CO.OCH$_2$—; and provided that, when $R^1$ stands for hydrogen, $R^2$ and $R^4$ stand for hydroxy radicals, and $R^3$ stands for a hydroxymethyl radical, $R^5$ does not stand for a hydroxymethyl radical; and, where appropriate, pharmaceutically-acceptable salts thereof.

It will be appreciated by those skilled in the art that, since the basic nucleus of the compounds of the invention contains several asymmetric centres, some of the compounds of the invention exist in diastereoisomeric forms. This is the case, for example, when $R^5$ contains at least one asymmetric centre, for example when $R^5$ stands for a 1-hydroxyethyl or α-hydroxybenzyl radical. Such diastereoisomeric forms can be separated from one another by conventional methods, for example by fractional crystallisation or chromatography.

$R^3$ may, for example, stand for a formyl or hydroxymethyl radical, or a group of the formula —CH$_2$O.CO.OR$^6$, wherein $R^6$ stands for a phenyl radical, or a phenyl radical which is substituted by an amino, methylamino, dimethylamino, carboxy or hydroxysulphonyl radical, or $R^6$ stands for a benzyl radical, or a benzyl radical which is substituted in the phenyl moiety by an amino, methylamino, dimethylamino, carboxy or hydroxysulphonyl radical.

$R^5$ may, for example, stand for a formyl, hydroxymethyl or 2-hydroxyethyl radical, or a radical of the formula —CHR$^7$OH, wherein $R^7$ stands for a methyl or phenyl radical, or a phenyl radical which is substituted by an amino, methylamino, dimethylamino, carboxy or hydroxysulphonyl radical, or $R^5$ may, for example, stand for an azidomethyl or pyrrolidin-2-ylcarbonyloxymethyl radical, or a group of the formula —CH$_2$O.CO.OR$^8$ wherein $R^8$ stands for a phenyl radical, or a phenyl radical which is substituted by an amino, methylamino, dimethylamino, carboxy or hydroxysulphonyl radical, or wherein $R^8$ stands for a benzyl radical, or a benzyl radical which is substituted in the phenyl moiety by an amino, methylamino, dimethylamino, carboxy or hydroxysulphonyl radical, or wherein $R^8$ stands for a piperidin-4-yl radical, or $R^5$ may, for example, stand for a group of the formula:

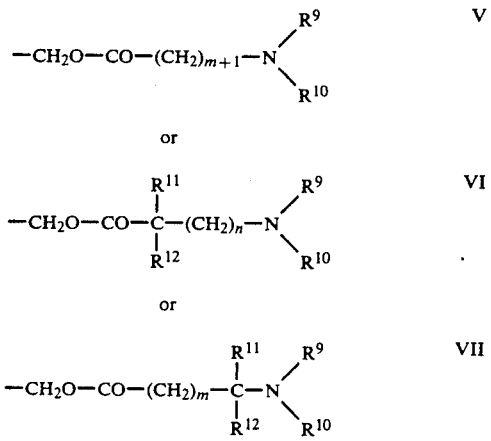

wherein m and n have the meanings stated above, $R^9$ stands for hydrogen or a methyl, phenyl, benzyl, t-butoxycarbonyl or benzyloxycarbonyl radical, and $R^{10}$ stands for hydrogen or a methyl radical, or $R^9$ and $R^{10}$ are joined to form, together with the adjacent nitrogen atom, a saturated N-linked heterocyclic radical of 5 or 6 ring atoms containing a nitrogen atom as a hetero-atom, for example such a radical containing a nitrogen atom as the sole hetero-atom, or containing two hetero-atoms consisting of two nitrogen atoms, or a nitrogen atom and an oxygen atom, or a nitrogen atom and a sulphur atom, for example a pyrrolidino, piperidino, piperazino or morpholino radical, and $R^{11}$ stands for hydrogen or a methyl, phenyl, tolyl, methoxyphenyl, benzyl, methylbenzyl or methoxybenzyl radical, and $R^{12}$ stands for hydrogen or a methyl radical, or wherein $R^5$ stands for a group of the formula -CH$_2$O.SO$_2$.R$^{13}$, wherein $R^{13}$ stands for a methyl, phenyl, p-tolyl, m-carboxyphenyl, naphthyl or dimethylaminonaphthyl, for example 5-dimethylaminonaphth-l-yl, radical.

One preferred embodiment of the invention consists of compounds of the formula II wherein $R^1$ stands for hydrogen, $R^2$ and $R^4$ stand for hydroxy radicals, $R^3$ stands for a hydroxymethyl radical, and $R^5$ stands for a group of the formula V wherein m, $R^9$ and $R^{10}$ have the meanings stated above, and more particularly wherein m stands for 0 or 1, $R^9$ stands for hydrogen, an alkyl radical of not more than 3 carbon atoms, an alkoxycarbonyl radical of not more than 6 carbon atoms, or a phenylalkoxycarbonyl radical of not more than 10 carbon atoms, and $R^{10}$ stands for hydrogen or an alkyl radical of not more than 3 carbon atoms, or wherein $R^9$ and $R^{10}$ are joined to form, together with the adjacent nitrogen atom, a saturated N-linked heterocyclic radical of 5 or 6 ring atoms containing a nitrogen atom as the sole hetero-atom, or containing two hetero-atoms consisting of two nitrogen atoms, or a nitrogen atom and an oxygen atom, or a nitrogen atom and a sulphur atom, and pharmaceutically-acceptable acid-addition salts thereof.

In the case where the compounds of the formula II are sufficiently basic, a suitable salt is an acid-addition salt derived from an inorganic or organic acid which affords a pharmaceutically-acceptable anion, for example hydrochloric or citric acid. In the case where the compounds of the formula II are sufficiently acidic, a suitable salt is a base-addition salt derived from a pharmaceutically-acceptable inorganic base, for example an alkali metal or alkaline earth metal salt, or an aluminium salt, or a salt derived from a pharmaceutically-acceptable organic base, for example trimethylamine, triethylamine, ethanolamine, ethylenediamine, morpholine or guanidine.

Aphidicolin and many of its derivatives have the disadvantage that they have any extremely low solubility in water. In the case of aphidicolin, for example, the aqueous solubility is 112±9 μg.per ml. Such a low solubility causes problems as regards the preparation of aqueous pharmaceutical formulations, for example aqueous formulations suitable for administration by injection, and therefore there is a need for water-soluble derivatives of aphidicolin.

According to a further feature of the invention there are provided water-soluble derivatives of aphidicolin, which are pharmaceutically-acceptable salts of compounds of the formula II wherein $R^1$ stands for hydrogen, $R^2$ and $R^4$ stand for hydroxy radicals, $R^3$ stands for a hydroxymethyl radical, and $R^5$ stands for a glycyloxymethyl, piperidin-4-yloxycarbonyloxymethyl, γ-(N-morpholino)-n-butyryloxymethyl, m-carboxybenzenesulphonyloxymethyl or 5-dimethylaminonaphthalenesulphonyloxymethyl radical. A preferred water-soluble compound is a pharmaceutically-acceptable salt, for example the hydrochloride, of a compound of the formula II wherein $R^1$, $R^2$, $R^3$ and $R^4$ have the meanings stated immediately above and $R^5$ stands for a glycyloxymethyl radical.

According to further features of the invention there are provided the following processes (it is to be understood that, unless otherwise stated, $R^1$, $R^2$, $R^3$ and $R^4$ have the meanings stated above):

(a) a process for the preparation of compounds of the formula II wherein $R^3$ stands for a hydroxymethyl radical and/or $R^5$ stands for a hydroxyalkyl radical of the formula $-(CH_2)_{1-3}OH$ and, where appropriate, pharmaceutically-acceptable salts thereof, which comprises hydrolysing the corresponding compound of the formula II wherein $R^3$ and/or $R^5$ contain(s) a t-butyldimethylsilyloxy radical;

(b) a process for the preparation of compounds of the formula II wherein at least one of $R^3$ and $R^5$ stands for a formyl radical and, where appropriate, pharmaceutically-acceptable salts thereof, which comprises oxidising the corresponding compound in which at least one of $R^3$ and $R^5$ stands for a hydroxymethyl radical;

(c) a process for the preparation of compounds of the formula II wherein $R^5$ stands for a radical of the formula $-CHR^7OH$, wherein $R^7$ stands for an alkyl radical of not more than 3 carbon atoms or a phenyl radical, which comprises reacting the corresponding compound wherein $R^5$ stands for a formyl radical with a lithium derivative of the formula $R^7Li$, wherein $R^7$ has the meaning stated immediately above, and reacting the intermediate lithium-containing product with water;

(d) a process for the preparation of compounds of the formula II wherein $R^5$ stands for a radical of the formula $-CH_2O.SO_2.R^{13}$, wherein $R^{13}$ has the meaning stated above, and, where appropriate, pharmaceutically-acceptable salts thereof, which comprises reacting the corresponding compound wherein $R^5$ stands for a hydroxymethyl radical with a compound of the formula $S^{13}.SO_2.Z$ wherein $R^{13}$ has the meaning stated above and Z stands for a halogen atom;

(e) a process for the preparation of compounds of the formula II wherein $R^5$ stands for an azidomethyl radical, which comprises reacting the corresponding compound, wherein $R^5$ stands for an alkanesulphonyloxymethyl radical of not more than 4 carbon atoms, or a benzenesulphonyloxymethyl or toluenesulphonyloxymethyl radical, with an alkali metal azide;

(f) a process for the preparation of compounds of the formula II wherein $R^4$ and $R^5$ are joined together to form the group $-O.CH_2-$, which comprises reacting the corresponding compound, wherein $R^5$ stands for an alkanesulphonyloxymethyl radical of not more than 4 carbon atoms, or a benzenesulphonyloxymethyl or toluenesulphonyloxymethyl radical, with an alkaline substance;

(g) a process for the preparation of compounds of the formula II wherein $R^5$ stands for a 2-hydroxyethyl radical, which comprises reacting the corresponding compound, wherein $R^4$ and $R^5$ are joined together to form the group $-O.CH_2-$, with n-butyl-lithium and the anion derived from 1,3-dithiane, and hydrolysing the resulting product, and then reacting the product thus obtained with an alkali metal borohydride;

(h) a process for the preparation of compounds of the formula II wherein at least one of $R^3$ and $R^5$ stands for a radical of the formula $-CH_2O.CO.OR^6$, wherein $R^6$ stands for a phenylalkyl radical of not more than 9 carbon atoms, which comprises reacting the corresponding compound, wherein at least one of $R^3$ and $R^5$ stands for a hydroxymethyl radical, with a compound of the formula $R^6O.CO.Z$, wherein Z has the meaning stated above and $R^6$ has the meaning stated immediately above;

(i) a process for the preparation of compounds of the formula II wherein either $R^5$ stands for a phenoxycarbonyloxymethyl radical or $R^4$ and $R^5$ are joined together to form the group of the formula $-O.CO.OCH_2-$, which comprises reacting the corresponding compound, wherein $R^4$ stands for a hydroxy radical and $R^5$ stands for a hydroxymethyl radical, with a compound of the formula $C_6H_5O.CO.Z$ wherein Z has the meaning stated above;

(j) a process for the preparation of compounds of the formula II wherein $R^5$ stands for a radical of the formula:

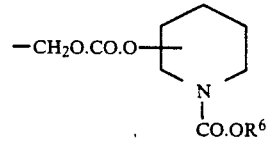

VIII wherein $R^6$ stands for a phenylalkyl radical of not more than 9 carbon atoms, which comprises reacting the corresponding compound wherein $R^5$ stands for a hydroxymethyl radical with a compound of the formula:

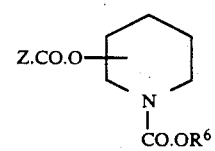

IX wherein Z has the meaning stated above, and $R^6$ has the meaning stated immediately above; (k) a process for the preparation of compounds of the formula II wherein $R^5$ stands for a piperidinyloxycarbonyloxymethyl radical, and pharmaceutically-acceptable acid-addition salts thereof, which comprises hydrogenolysing the corresponding compound wherein $R^5$ stands for a radical of the formula VIII wherein $R^6$ has the meaning stated above;

(1) a process for the preparation of compounds of the formula II wherein $R^5$ stands for a group of the formula IV, and pharmaceutically-acceptable acid-addition salts thereof, which comprises reacting the corresponding compound wherein $R^5$ stands for a hydroxymethyl radical with an acid of the formula $R^9R^{10}N(CH_2)_n.CR^{11}R^{12}.(CH_2)_m.CO_2H$, or an acid halide or anhydride thereof, and wherein m, n, $R^9$, $R^{10}$, $R^{11}$ and $R^{12}$ have the meanings stated above;

(m) a process for the preparation of compounds of the formula II wherein $R^2$ and $R^3$, and $R^4$ and $R^5$, are joined together to form the group of the formula $-O.CO.OCH_2-$, which comprises reacting aphidicolin with phosgene;

(n) a process for the preparation of compounds of the formula II wherein $R^5$ stands for a group of the formula $-CH_2O.CO.(CH_2)_m.CR^{11}R^{12}.(CH_2)_n.NHR^{14}$, and pharmaceutically-acceptable acid-addition salts thereof, which comprises hydrogenolysing a corresponding compound, wherein $R^5$ stands for a group of the formula $-CH_2O.CO.(CH_2)_m.CR^{11}R^{12}.(CH_2)_n.N(R^{14})CO_2R^{15}$, wherein $m, n, R^{11}$ and $R^{12}$ have the meanings stated above, $R^{14}$ stands for hydrogen, an alkyl radical of not more than 6 carbon atoms, or an aryl radical of not more than 10 carbon atoms, and $R^{15}$ stands for an α-phenylalkyl radical of not more than 9 carbon atoms;

(o) a process for the preparation of compounds of the formula II wherein $R^5$ stands for a group of the formula $-CH_2O.CO.(CH_2)_m.CR^{11}R^{12}.(CH_2)_n.NHR^{14}$, and pharmaceutically-acceptable acid-addition salts thereof, which comprises selectively hydrolysing, under acidic conditions, the corresponding compound wherein $R^5$ stands for a group of the formula $-CH_2O.CO.(CH_2)_m.CR^{11}R^{12}.(CH_2)_n.N(R^{14}).CO_2C_4H_9^t$, and wherein $m, n, R^{11}, R^{12}$ and $R^{14}$ have the meanings stated above.

In process (a) the hydrolytic agent may be a suitable inorganic or organic acid, for example hydrochloric acid or trifluoroacetic acid. The hydrolysis is preferably carried out in the presence of an organic solvent, for example ethanol, and at or below ambient temperature.

In process (b) the oxidising agent may, for example, be N,N-dicyclohexylcarbodiimide, and the oxidation may be carried out in an organic solvent, for example a mixture of dimethyl sulphoxide and benzene, and in the presence of pyridine and trifluoroacetic acid.

The first stage of process (c) is conveniently carried out in an organic solvent, for example tetrahydrofuran.

In processes (d), (h), (i) and (j), Z may, for example, stand for a chlorine or bromine atom, and each of these processes is conveniently carried out in pyridine.

In process (e) a suitable alkali metal azide is, for example, sodium azide. The process is carried out in a suitable organic solvent, for example dimethylformamide, and it may be accelerated or completed by the application of heat.

In process (f) the alkaline substance may, for example, be an ion-exchange resin in alkaline form, for example a strongly basic ion-exchange resin, or an alkali metal hydride, for example sodium hydride, or an alkali metal $C_{1-6}$-alkoxide, for example potassium t-butoxide. The process involving an ion-exchange resin is conveniently carried out in a suitable solvent, for example an aqueous $C_{1-3}$-alkanol, for example aqueous methanol. The process involving a hydride or an alkoxide is conveniently carried out in a suitable solvent, for example an ether, for example diethyl ether or tetrahydrofuran.

The first stage of process (g) is carried out in a suitable organic solvent, for example tetrahydrofuran. A suitable borohydride for use in the second stage is sodium borohydride.

Processes (k) and (n) are carried out by reacting the starting material with hydrogen gas in the presence of a hydrogenation catalyst, for example a palladium-on-charcoal catalyst. The processes are carried out in an organic solvent, for example an alkanol of not more than 3 carbon atoms, for example ethanol, or an alkyl alkanoate of not more than 8 carbon atoms, for example ethyl acetate, at ambient temperature and at atmospheric pressure or a slightly elevated pressure.

In process (1) the acid halide may, for example, be an acid chloride or bromide, and the acid anhydride may either be derived wholly from the parent acid (i.e. of the type R—CO—O—CO—R) or it may be a mixed anhydride obtained in conventional manner. The process may be carried out in an organic solvent, for example pyridine.

Process (m) is conveniently carried out in an organic solvent, for example pyridine.

Process (o) may be carried out by, for example, the use of hydrogen chloride or trifluoroacetic acid as the hydrolytic agent. It may be carried out in a mixture of water and an organic solvent containing a relatively substantial amount of water, or in an organic solvent, for example diethyl ether, containing a very small amount of water.

The acid-addition salts of the invention are obtainable by conventional procedures. Aphidicolin, which is used as a starting material in some of the processes of the invention, is obtainable as described in United Kingdom patent specification No. 1,331,520. Other starting materials are obtained as described below.

The antiviral activity of compounds of the invention has been demonstrated against *Herpes simplex in vitro*. The anti-tumour activity of compounds of the invention has been demonstrated against the mouse $C_{26}$ colonic tumour. The potency of any particular compound depends upon its chemical structure, but generally speaking the compounds of the invention exhibit antiviral activity *in vitro* at a concentration in the range 0.01 to 50 μg./ml. and they exhibit activity in vivo against the mouse $C_{26}$ colonic tumour at a dose in the range 25 to 200mg./kg. No toxic effects have been observed with the compounds of the invention at doses at which they exhibit activity in the abovementioned tests. For example, this is the case with the compound of Example 21 at an effective dose (75 mg./kg. intraperitoneally) against the mouse $C_{26}$ colonic tumour.

According to a further feature of the invention there are provided pharmaceutical compositions comprising a compound of the formula II, wherein $R^1, R^2, R^3, R^4$ and $R^5$ have the meanings stated above, or, where appropriate, a pharmaceutically-acceptable salt thereof, and a pharmaceutically-acceptable diluent or carrier.

The compositions of the invention may, for example, be in a suitable form for oral, parenteral or rectal administration. Thus, for example, they may be in an orally-administrable unit dosage form, for example a tablet or capsule, which may optionally be adapted for sustained or controlled release, or they may be in an injectable form, for example a sterile injectable solution or suspension, or in the form of a suppository.

The pharmaceutical compositions of the invention are obtainable by conventional methods using conventional diluents and carriers.

The invention is illustrated but not limited by the following Examples in which the temperatures are expressed in degrees Celsius and the nomenclature is based on the parent hydrocarbon (aphidicolane) having the following structure and numbered as shown (see J.C.S. Chem. Comm., 1972, 1027):

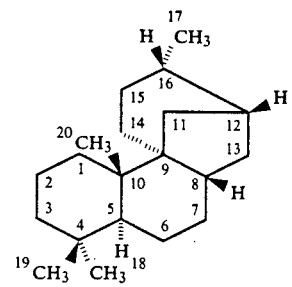

Unless otherwise stated, the expression "in vacuo" means that the pressure used was approximately 12mm. (water pump pressure).

EXAMPLE 1

17,18-Bis(t-butyldimethylsilyloxy)-16$\beta$-hydroxy-3-oxo-aphidicolane (6.0 g., 0.106 mole) was dissolved in ethanol (60 ml.), and 4N-hydrochloric acid (6 ml.) was added. The mixture was refluxed for 25 min., cooled, and neutralised with saturated sodium bicarbonate solution. The solvent was evaporated in vacuo and the residue was shaken together with a mixture of ethyl acetate (200 ml.) and water (200 ml.). The mixture was separated, both phases being retained. The aqueous phase was extracted with ethyl acetate (2×50m.). The combined organic phases were dried (Na$_2$SO$_4$), the solvent was evaporated in vacuo, and the residual white solid was chromatographed on silica gel (Merck Art. 9385; column 5cm.×18cm.), eluting with ethyl acetate:methanol 19:1 v/v and collecting 30 ml. fractions. The fractions shown by thin layer chromatography ("t.l.c.") to contain the desired product were evaporated in vacuo to give 16$\beta$,17,18-trihydroxy-3-oxo-aphidicolane, m.p. 152°-3°. A small sample was recrystallised from ethyl acetate and had m.p. 152.5°-3°.

The compound used as starting material was obtained as follows:

Aphidicolin (16.9 g., 0.05 mole) was dissolved in dry pyridine (250 ml.), the solution was stirred, and imidazole (18.1 g. 0.25mole) was added. Dry pyridine (250 ml.) was added, and the resulting solution was protected from atmospheric moisture (drying tube). t-Butyldimethylchlorosilane (17.6 g., 0.12mole) was added over 1.5 hr. to the stirred solution, and stirring was continued for a further 30 min. Most of the pyridine was then evaporated in vacuo and the residue was shaken together with ether (750 ml.) and water (750 ml.). The mixture was separated, both phases being retained. The aqueous phase was extracted with ether (2×250 ml.) and the combined organic phases were dried (Na$_2$SO$_4$) and the solvent evaporated in vacuo to give a white solid as the residue. This was chromatographed on silica gel (Merck Art. 9385; column 5cm.×25cm.), eluting with a 1:1 v/v mixture of ether and petroleum ether (b.p. 40°-60°) and collecting 100 ml. fractions. Fractions 5 to 9 were combined and evaporated in vacuo to give 17,18-bis(t-butyldimethylsilyloxy)-3$\alpha$,16$\beta$-dihydroxyaphidicolane, m.p. 116°-8°. A small sample was recrystallised from petroleum ether (b.p. 40°-60°) and had m.p. 121°-2°.

A mixture of the last-named aphidicolane derivative (6.0 g., 0.0106 mole), pyridinium chlorochromate (4.8 g., 0.022 mole) and sodium acetate (1.5 g., 0.018mole) in methylene dichloride (25 ml.) was stirred at ambient temperature for 4 hours. Ether (100 ml.) was added, and the supernatant solution was decanted from the black residue. The residue was washed with ether (2×50 ml.) and the combined organic washings were passed through a column of magnesium silicate ['Florisil' (Trade Mark); column ¼"×7"], the column being washed with ether (50 ml.). The eluate was evaporated in vacuo to dryness. The residue was chromatographed on a silica column (Merck Art. 9385; column ¼"×7"), eluting with a gradient of ether:petroleum ether (b.p. 40°-60°) and collecting 350 ml. fractions. The fractions eluted with 3:7 v/v ether:petroleum ether contained the desired product, and these fractions were combined and evaporated in vacuo to give 17,18-bis(t-butyldimethylsilyloxy)-16-hydroxy-3-oxo-aphidicolane, m.p. 116°-8°. A small sample was crystallised from petroleum ether (b.p. 40°-60°) and then had m.p. 118°-9.5°.

EXAMPLE 2

17,18-Bis(t-butyldimethylsilyloxy)-3$\beta$,16$\beta$-dihydroxy-3$\alpha$-methylaphidicolane (0.2097 g., 0.000362 mole) was dissolved in tetrahydrofuran (10 ml.), and a solution of tetra-n-butylammonium fluoride (0.4608 g.; 0.001458 mole) in tetrahydrofuran (2.5 ml.) was added with stirring at ambient temperature. After one hour the mixture was poured into water (100 ml.) and extracted with ethyl acetate (4×25 ml.). The combined extracts were dried (Na$_2$SO$_4$) and the solvent was evaporated in vacuo. The residual solid was triturated with ether (4×2 ml.) to give 3$\beta$,16$\beta$,17,18-tetrahydroxy-3$\alpha$-methylaphidicolane, m.p. 220°-230°. A small sample was crystallised from ethyl acetate:methanol 9:1 v/v and then had m.p. 244°-8°.

The compound used as starting material was obtained as follows:

17,18-Bis(t-butyldimethylsilyloxy)-16$\beta$-hydroxy-3-oxo-aphidicolane (0.60 g.; 0.00106 mole) was dissolved in dry ether (4 ml.), and the solution was added to methyl magnesium iodide, which had been prepared in the usual manner from magnesium (0.0703 g., 0.00293 g. atom) and methyl iodide (0.360 g., 0.158$\mu$l., 0.00254 mole) in dry ether (10 ml.). The mixture was stirred for one hour and then allowed to stand overnight. The reaction mixture was poured into water (100 ml.) and the mixture was extracted with ethyl acetate (4×20 ml.). The combined extracts were dried (Na$_2$SO$_4$) and the solvent was evaporated in vacuo. The residue was chromatographed on silica gel (Merck Art. 9385, 40 g.), eluting with ethyl acetate:toluene 1:9 v/v and collecting 5 ml. fractions. There was thus obtained 17,18-bis-(t-butyldimethylsilyloxy)-3$\beta$,16$\beta$-dihydroxy-3$\alpha$-methylaphidicolane, m.p. 105°-7°. (It has not been rigorously proved that the two 3$\beta$-hydroxy-3$\alpha$-methyl derivatives described in this Example actually have the structure indicated, although this is considered likely. However, the compounds may in fact be 3$\alpha$-hydroxy-3$\beta$-methyl derivatives.)

EXAMPLES 3 AND 4

Aphidicolin (3.4016 g., 0.101 mole) was dissolved in dimethyl sulphoxide, and benzene (25 ml.), pyridine (1.23 ml., 1.20 g., 0.152 mole) and trifluoroacetic acid (0.385 ml., 0.570 g., 0.00499 mole) were added successively. The mixture was protected from atmospheric moisture (drying tube) and stirred at ambient temperature. N,N-Dicyclohexylcarbodiimide (6.2818 g., 0.305 mole) was added and the mixture was stirred overnight at ambient temperature. The solvent was evaporated in vacuo and the residue was stirred together with ethyl acetate (100 ml.). The mixture was filtered and the solvent in the filtrate was evaporated in vacuo. The residue was chromatographed on silica gel (Merck Art. 9385, 250 g.), eluting with ethyl acetate and collecting 25 ml. fractions. Fractions 18 to 24 were combined and re-chromatographed on silica gel (Merck Art. 9385, 100 g.), eluting with ethyl acetate:toluene 2:3 v/v and collecting 10 ml. fractions. The fractions containing the desired product (detected by tlc) were combined and evaporated in vacuo to give 3$\alpha$,16$\beta$-dihydroxyaphicolan-17,18-dial (Example 3) as a colourless gum, NMR (CDCl$_3$ solution, 90 MHz):.46 $\tau$(1H,s), .51 $\tau$(1H,s), 6.3 $\tau$ (1H, broad s), 9.03 $\tau$(3H,s), and 9.08$\tau$(3H,s).

Fractions 28 to 32 from the first column were combined and re-chromatographed on silica gel (Merck Art. 9385, 100 g.), eluting with ethyl acetate: toluene 4:1 v/v and collecting 10 ml. fractions. The fractions containing the desired product (detected by tlc) were combined and evaporated in vacuo to give a colourless gum (A). Fractions 33 to 40 from the first column were combined and the solvent evaporated in vacuo to give a colourless gum (B). The gums A and B were combined, and there was thus obtained 3α, 16β, 18-trihydroxyaphidicolan-17-al (Example 4) as a colourless gum, NMR (CDCl$_3$ solution plus D$_2$O, 90 MHz): .32 (1H,s), 6.33 (1H, broad s), 6.4–6.8 (2H, AB quartet, J=13.5 Hz).

EXAMPLE 5

A solution of 3α,16β,18-trihydroxyaphidicolan-17-al (0.0677 g., 0.0002 mole) in dry tetrahydrofuran (5 ml.) was stirred and cooled to 0° under a nitrogen atmosphere. A 1.67M solution of phenyl lithium (1 ml., 0.00167 mole) in ether:benzene 30:70 v/v was added, and the mixture was allowed to warm to ambient temperature and then stirred overnight. The mixture was cooled to 0°, water (1 ml.) was added, the resulting mixture was poured into water (50 ml.), and the mixture thus obtained was extracted with ethyl acetate (4×25 ml.). The combined extracts were dried (Na$_2$SO$_4$) and the solvent evaporated in vacuo. The residue showed two distinct spots (R$_f$ 0.32 and 0.52) on silica gel tlc (Merck Art. 5715), eluting with ethyl acetate. The two diastereoisomers isomers were separated by chromatography on silica gel (Merck Art. 9385, 50 g.), eluting with ethyl acetate and collecting 5 ml. fractions. The appropriate fractions were ascertained by tlc, combined, and evaporated in vacuo. There were thus obtained two diastereoisomeric forms of 3α,16β,17,18-tetra-hydroxy-17-phenylaphidicolane:

Diastereoisomer (a) (the less polar compound, R$_f$ 0.52), NMR (CDCl$_3$ plus D$_2$O, 90 MHz): 2.82 τ (5H,s), 5.49 τ (1H,s), 6.36τ (1H, broad s), 6.40–6.80 τ (2H, AB quartet J=13.1 Hz), 9.04 τ (3H,s) and 9.33 τ (3H,s).

Diastereoisomer (b) (the more polar compound, R$_f$ 0.32), NMR (CDCl$_3$ solution plus D$_2$O, 90 MHz): 2.63 τ (5H,s), 5.34τ (1H,s), 6.30 τ (1H, broad s); 6.38–6.74 τ (2H, AB quartet, J=13.1 Hz), 9.08 τ (3H,s) and 9.32 τ (3H,s).

EXAMPLE 6

A solution of 3α,16β,18-trihydroxyaphidicolan-17-al (0.1344 g. 0.0004 mole) in dry tetrahydrofuran (5 ml.) was stirred and cooled to 0° under a nitrogen atmosphere. A 1.4M solution of methyl lithium (2.2 ml., 0.0031 mole) in diethyl ether was added, and the mixture was allowed to warm up to ambient temperature and then stirred overnight. The mixture was cooled to 0°, water (1 ml.) was added, the mixture was poured into water (25 ml.), and the resulting mixture was extracted with ethyl acetate (4×25 ml.). The combined extracts were dried (Na$_2$SO$_4$) and the solvent evaporated in vacuo. The residue was a colourless gum showing two distinct spots (R$_f$0.16 and 0.22) on silica gel tlc (Merck Art. 5715), eluting with ethyl acetate. The two diastereoisomers were separated by chromatography on silica gel (Merck Art. 9385, 50 g.), eluting with ethyl acetate and collecting 5 ml. fractions. The appropriate fractions were ascertained by tlc, combined, and evaporated in vacuo. There were thus obtained two diastereoisomeric forms of 3α,16β,17,18-tetrahydroxy-17-methylaphidicolane:

Diastereoisomer (a) (the less polar compound, R$_f$ 0.22) softened on heating at 210°-218° and had m.p. 218°-221°. A small sample was crystallised from ethyl acetate, and on heating this softened at 210°-217° and had m.p. 217°-220°.

Diastereoisomer (b) (the more polar component, R$_f$0.16) had-m.p. 180°-3°. A small sample was crystallised from ethyl acetate and had m.p. 183°-6°.

EXAMPLE 7

Aphidicolin (6.78 g., 0.201 mole) was dissolved in pyridine (250 ml.) and the solution was cooled in ice. p-Toluenesulphonyl chloride (5.77 g., 0.0302 mole) was added portionwise over 4 hours and the reaction mixture was protected from atmospheric moisture with a drying tube. The mixture was kept at 4° overnight. Water (10 ml.) was added and the mixture was evaporated in vacuo (ca. 0.1 mm., dry ice cold finger). The residue was shaken together with ethyl acetate (250 ml.), and the mixture was separated, both phases being retained. The aqueous phase was extracted with ethyl acetate (2×250 ml.). The combined organic phases were washed with N-hydrochloric acid until they were neutral, then with water (4×100 ml.), and then they were dried (Na$_2$SO$_4$). The solvent was evaporated in vacuo and the residual white foam was chromatographed on silica gel (Merck Art. 9385, 100 g.), eluting with ethyl acetate : toluene 1:1 v/v and collecting 10 ml. fractions. The fractions containing the desired product (detected by tlc) were combined and evaporated in vacuo to give 3α, 16β,18-trihydroxy-17-p-toluenesulphonyloxyaphidicolane, m.p. 142°-4°.

EXAMPLE 8

Sodium azide (0.1370 g. 0.00021 mole) was added to a solution of 3α,16β,18-trihydroxy-17-p-toluenesulphonyloxyaphidicolane (0.1014 g., 0.00021 mole). The mixture was heated at 100° for 4 hours and then cooled and the solvent evaporated in vacuo (0.1 mm. pressure; solid CO$_2$ cold finger condenser). The residue was shaken together with ethyl acetate (25 ml.) and water (25 ml.), and the mixture was separated, both phases being retained. The aqueous phase was extracted with ethyl acetate (2×25 ml.), and the combined organic phases were washed with water (2×25 ml.), dried (Na$_2$SO$_4$) and the solvent evaporated in vacuo. The residue was chromatographed on silica gel (Merck Art. 9385, 10 g.), eluting with ethyl acetate and collecting 5 ml. fractions. The fractions containing the desired product (detected by tlc) were combined and evaporated in vacuo to give a gum which crystallised on adding ether to give 3α,16β, 18-trihydroxy-17-azidoaphidicolane, m.p. 145°-7°. A small sample was recrystallised from ether and had m.p. 147°-8°.

EXAMPLE 9

3α,16β,18-Trihydroxy-17-p-toluenesulphonyloxyaphidicolane (8.5 g.) was dissolved in methanol : water (9:1 v/v, 1l.). 'Amberlite' (Trade Mark) ion-exchange resin (IRA 400, 75 g.) in its basic form was added and the mixture was heated under reflux until the assay showed that there was no further reaction (30 mins). The mixture was filtered, the filtrate was evaporated in vacuo to a volume of approx. 200 ml. and water (300 ml.) was added. The solution was extracted with ethyl acetate (3×200 ml.), the combined extracts were washed with water and dried (Na$_2$SO$_4$), and the solvent was evaporated in vacuo. The residue was chromatographed on silica gel (Merck Art. 9385, 125 g.), eluting with ethyl acetate: toluene 1:1 v/v and collecting 10 ml. fractions. The fractions containing the desired product (detected by tlc) were combined and the solvent evaporated in vacuo. The solid residue was crystallised from ether to give 16β,17-epoxy-3α,18-dihydroxyaphidicolane, m.p. 141°-3°.

EXAMPLE 10

1,3-Dithiane (0.40 g. 0.00333 mole) was dissolved in tetrahydrofuran (10 ml.), and the solution was cooled to −20° under a nitrogen atmosphere. A solution of n-butyl lithium in n-hexane (2.08 ml. of a 1.60M-solution, 0.00333 mole) was added to the stirred 1,3-dithiane solution at −20°, and stirring at −20° was continued for 90min. A solution of 16β,17-epoxy-3α,18-dihydroxyaphidicolane (0.1073 g., 0.000335 mole) was added to the stirred mixture at −20°, and the resulting mixture was stirred at −20° for 1 hr. and then at ambient temperature for 2 hrs. The mixture was poured into water (100 ml.) and the resulting mixture was extracted with ethyl acetate (4×25 ml.). The combined extracts were dried ($Na_2SO_4$) and the solvent was evaporated in vacuo to give the crude dithiane adduct which was chromatographed on silica gel (Merck Art. 9385, 10 g.), eluting with ethyl acetate and collecting 1 ml. fractions. The fractions containing the desired intermediate (detected by tlc) were combined and the solvent evaporated in vacuo to give a partially purified intermediate which was used directly in the next stage.

The intermediate (0.1634 g.) was dissolved in tetrahydrofuran (2 ml.), and the solution was added to a stirred mixture of red mercuric oxide (0.16 g., 0.000739 mole) and boron trifluoride etherate (0.160 ml.) in tetrahydrofuran:water 9:1 v/v (15 ml.). The mixture was stirred for 30 min. at ambient temperature, cooled to 0°, and to it was added a solution of sodium borohydride (0.20 g., 0.00526 mole) in water (1 ml.). The resulting mixture was filtered (Celite; Trade Mark), the solid residue being washed successively with ethyl acetate (2×10 ml.) and water (2×10 ml.). The combined filtrate and washings were diluted with water (100 ml.) and extracted with ethyl acetate (4×25 ml.). The combined extracts were dried ($Na_2SO_4$) and the solvent evaporated in vacuo. The residue was chromatographed on silica gel (Merck Art. 9385, 10 g.), eluting with ethyl acetate: methanol 9:1 v/v and collecting 1 ml. fractions. The fractions containing the desired compound (detected by tlc) were combined and the solvent evaporated in vacuo to give a white solid which was crystallised from ethyl acetate:methanol (9:1 v/v, 1 ml.) to give white plates of m.p. 185°-7°. A small sample was recrystallised from ethyl acetate to give 3α,16β,18-trihydroxy-17-hydroxymethylaphidicolane, m.p. 187°-8°.

EXAMPLES 11 and 12

Aphidicolin (6.76 g., 0.02 mole) was dissolved in dry pyridine (100 ml.) and the solution was protected from atmospheric moisture (drying tube) and stirred and cooled in ice. Benzyl chloroformate (7.15 ml., 8.58 g., 0.05mole) was added in three portions over 30 min. The solution was then stood in ice for 1.5 hr. Periodic acid (5 ml.) was added, and the pyridine was evaporated in vacuo (0.1 mm pressure; solid $CO_2$ cold finger condenser). The residue was shaken together with water (100 ml.) and ethyl acetate (100 ml.), and the mixture was separated, both phases being retained. The aqueous phase was extracted with ethyl acetate (3×50 ml.). The combined organic phases were washed with N-hydrochloric acid (4×25 ml.) then with water (portions of 25 ml.) to pH 7, and then dried ($Na_2SO_4$). The solvent was evaporated in vacuo and chloroform (50 ml.) was again added, and the solvent was evaporated in vacuo to a volume of approx. 20 ml., whereupon a solid separated. Chloroform:petroleum ether (b.p. 60°-80°) 1:1 v/v (50 ml.) was added to the mixture, the resulting mixture was filtered, and the solid residue was washed with the same solvent mixture (3×10 ml.). There was thus obtained 17-benzyloxy-carbonyloxy-3α, 16β, 18-trihyroxyaphidicolane (Example 11), NMR ($CDCl_3$ solution plus $D_2O$, 90 MHz): 2.64τ(5H,s), 4.85τ(2H,s), 5.97τ(2H,s), 6.35 τ(1H, broad s), 6.44°-6.84°τ(2H, AB quartet, J=10.8 Hz), 9.04τ(3H,s) and 9.32τ(3H,s).

The mother liquors from the above crystallisation. were evaporated in vacuo and the residue was chromatographed on silica gel (Merck Art. 9385), eluting with ethyl acetate:toluene 1:1 v/v and collecting 25 ml. fractions. Fractions 9 to 11 were combined and the solvent evaporated in vacuo to give 17,18-bis(benzyloxycarbonyloxy)-3α,16β-dihydroxyaphidicolane (Example 12) as a colourless gum, NMR ($CDCl_3$ plus $D_2O$, 90 MHz): 2.62τ(10H, s), 4.84 τ(4H,s), 5.7°-6.1τ(2H, AB quartet, J=9.9 Hz), 5.97 (2H, s), 6.38τ(1H, broad s), 9.05τ(3H,s) and 9.09τ(3H,s).

Fractions 21 to 35 from the abovementioned column were combined and the solvent evaporated in vacuo, and there was obtained a further quantity of the said mono-benzyloxycarbonyloxy derivative.

EXAMPLES 13 AND 14

Aphidicolin (0.3432 g., 0.00102 mole) was dissolved in dry pyridine (5 ml.) and the solution was protected from atmospheric moisture (drying tube) and stirred and cooled in ice. Phenyl chloroformate (0.157 g., 0.127 ml., 0.001 mole) was added over 15 min. Water (1 ml.) was then added and the solvents were evaporated in vacuo. The residue was chromatographed on silica gel (Merck Art. 9385, 25 g.), eluting with ethyl acetate and collecting 5 ml. fractions. Fractions 14 to 21 were combined and the solvent evaporated in vacuo. The residue was crystallised from ethyl acetate to give 3α,16β,18-trihydroxy-17-phenyloxycarbonyloxyaphidicolane (Example 13), NMR (CDCl plus $D_2O$, 90 MHz): 2.4°-2.9°τ(5H, m), 5.83τ(2H,s), 6.30τ(1H, broad s), 6.42°-6.80°τ(2H, AB quartet, J=11.7 Hz), 9.01τ (3H,s) and 9.30τ(3H,s).

The mother liquor from the abovementioned crystallisation was evaporated in vacuo. The residue was dissolved in toluene (5 ml.) and the solution heated under reflux for 30 min. The solvent was evaporated in vacuo and the residue crystallised from ether to give aphidicolin 16β,17-monocarbonate, m.p. 221°-5°. A small sample was crystallised from ethyl acetate and had m.p. 225°-6.5°.

EXAMPLE 15

Aphidicolin (3.4 g., 0.01 mole) was dissolved in dry pyridine (50 ml.) and the solution was protected from atmospheric moisture (drying tube) and stirred and cooled in ice. 1-Benzyloxy-carbonyl-4-chlorocarbonyloxypiperidine (4 ml.) was added to the stirred solution in 1 ml. portions over 1 hr. The solvent was evaporated in vacuo (1 mm. pressure, solid $CO_2$ cold finger condenser). The residue was shaken together with ethyl acetate (100 ml.) and water (100 ml.), and the mixture was separated, both phases being retained. The aqueous phase was extracted with ethyl acetate (2×100 ml.). The combined organic extracts were dried (Na$_2$SO$_4$) and the solvent evaporated in vacuo. The residue was chromatographed on silica gel (Merck Art. 9385, 250 g.), eluting with ethyl acetate:toluene 3:2 v/v and collecting 20 ml. fractions. Fractions 45 to 97 were combined and the solvent evaporated in vacuo to give 17-[1-(benzyloxycarbonyl)piperidin-4-yloxycarbonyloxy]-3α,16β,18-trihydroxyaphidicalone as a waxy solid, NMR (CDCl$_3$ solution, 90MHz) : 2.64τ (5H,s), 4.88τ(2H,s), 5.24τ(1H, 7 line multiplet), 5.99τ(2H,s), 6.07-6.30τ(2H,m), 6.35τ(1H, broad s), plus D$_2$O : 6.5-7.1τ(4H,m), 9.04 τ(3H,s) and 9.32 τ(3H,s).

The benzyloxycarbonyl derivative used as starting material was obtained as follows:

4-Hydroxypiperidine (10 g., 0.099 mole) and N,N-diisopropylethylamine (87 ml., 0.495 mole) were dissolved in methylene dichloride (200 ml.). The solution was cooled (ice bath) and protected from atmospheric moisture (drying tube), and benzyl chloroformate (14.1 ml., 16.9 g., 0.099 mole) was added over 2 hrs. Water (20 ml.) was added and the solvents were evaporated in vacuo (approx. 1 mm. pressure, solid CO$_2$ cold finger condenser). The residue was shaken together with water (200 ml.) and ethyl acetate (200 ml.), and the mixture was separated. The organic phase was washed with water (4×50 ml.), dried (Na$_2$SO$_4$), and the solvent evaporated to give 1-benzyloxycarbonyl-4-hydroxypiperidine as a colourless oil, I.R.μmax 3800 cm.$^{-1}$ and 1685cm.$^{-1}$.

1-Benzyloxycarbonyl-4-hydroxypiperidine (15 g., 0.0638 mole) and N,N-diisopropylethylamine (12.3 ml., 9.13 g., 0.0707 mole) were dissolved in toluene (150 ml.), and the solution was added over 30 min. to a solution. of phosgene (12.63 g., 0.128 mole) in toluene (150 ml.). The reaction mixture was protected from atmospheric moisture (drying tube), stirred magnetically, and kept at ambient temperature in a water bath during the addition. When the addition was complete the mixture was filtered and the solid residue washed with toluene (ca. 50 ml.). The solvent in the combined filtrate and washings was evaporated in vacuo (1 mm. pressure, solid CO$_2$ cold finger condenser) to give 1-benzyloxycarbonyl-4-chlorocarbonyloxypiperidine, I.R. λ max 1775cm.$^{-1}$ and 1700 cm.$^{-1}$.

EXAMPLE 16

17-[1-(Benzyloxycarbonyl)piperidin-4-yloxycarbonyloxy]-3α,16β,18-trihydroxyaphidicolane, (3.0028 g., 0.00501 mole) was dissolved in ethanol (25 ml.) and the solution added to a suspension of 30% w/w palladium-on-charcoal catalyst (0.2997 g.) in ethanol (100 ml.) containing N-hydrochloric acid (10 ml.). The mixture was hydrogenated at ambient temperature and atmospheric pressure for 2 hr. The catalyst was removed by filtration (Celite; Trade Mark), the solvent in the filtrate was evaporated in vacuo (1 mm. pressure, solid CO$_2$ cold finger condenser), ethanol (20 ml.) was added to the residue, and the solvent evaporated in vacuo. The residue was then freeze-dried from water (200 ml.) to give 3α,16β,18-trihydroxy-17-piperidin-4-yloxycarbonyloxyaphidicolane hydrochloride, NMR (d$_5$ pyridine solution, 90 MHz): 2.2-3.8τ(ca. 8H, very broad s, exchanged with D$_2$O), 4.94τ(1H, broad s), 5.63τ (2H,s), 6.1τ (1H, broad s), 6.1-6.5τ(2H, AB quartet), 6.4-6.9τ(4H, broad m), 9.0τ(3H,s) and 9.23τ(3H,s).

EXAMPLE 17

γ-(1-Morpholino)butyric acid hydrochloride (2.2895 g., 0.109 mole) was dissolved in pyridine (50 ml.), N-methylmorpholine (4.46 ml., 4.04 g., 0.04 mole) was added, and the solution was cooled in an ice-salt mixture (internal temperature −10°). The mixture was stirred rapidly and benzenesulphonyl chloride (1.28 ml., 1.77 g., 0.01 mole) was added dropwise over 15 min The mixture was added to a solution of aphidicolin (1.689 g., 0.005 mole) in pyridine (50 ml.), itself cooled in an ice-salt mixture. The mixture was stirred with cooling for 2 hr. and then allowed to warm to ambient temperature. Water (5 ml.) was added and the solvents evaporated in vacuo (1 mm. pressure, solid CO$_2$ cold finger condenser). The residue was shaken together with ethyl acetate (100 ml.) and water (100 ml.), and the mixture was separated, both phases being retained. The aqueous phase was extracted with ethyl acetate (2×100 ml.), and the combined organic phases were extracted with 0.4N-hydrochloric acid (3×50 ml.). The combined aqueous extracts were washed with ethyl acetate (2×50 ml.), neutralised first with solid sodium bicarbonate and finally to pH 9 with saturated aqueous sodium carbonate solution. The aqueous solution was extracted with ethyl acetate (3×100 ml.), the combined extracts dried (Na$_2$SO$_4$) and the solvent evaporated in vacuo to give 3α,16β,18-trihydroxy-17-(γ-morpholino-n-butyroxy)aphidicolane as a gum which crystallised on the addition of ether and then had m.p. 157°-8°. A small sample was crystallised from ethyl acetate and had m.p. 159°.

The hydrochloride was prepared by dissolving the free base in methanol:water (1 g. of the base to 25 ml. of methanol and 50 ml. of water) and titrating the solution to pH 6 with 0.1N-hydrochloric acid. The solvent in the resulting solution was evaporated in vacuo (0.1 mm. pressure, solid CO$_2$ cold finger condenser) to a volume of approx. 50 ml., and the residue was freeze-dried. The hydrochloride was obtained as a voluminous white solid, NMR (d$_5$ pyridine solution, 90 MHz): 2.86τ(ca. 6H, broad s, exchanged with D$_2$O), 5.67τ(2H,s), 5.77-6.02τ (4H, m), 6.06τ(1H, broad s), 6.08-6.50τ(2H, AB quartet, J=10.8 Hz), 6.80-7.10τ(4H,m), 9.0τ (3H,s) and 9.21τ(3H,s).

EXAMPLE 18

Aphidicolin (0.056 g., 0.000166 mole) was dissolved in pyridine (5 ml.) and phosgene gas was bubbled through the solution until tlc assay (Merck Art. 5715) indicated that no starting material remained. The mixture was poured onto ice (50 g.), the mixture extracted with ethyl acetate (4×25 ml.), and the combined extracts dried (Na$_2$SO$_4$). The solvent was evaporated in vacuo to give aphidicolin 3α,18;16β, 17-biscarbonate, m.p. 290°-300°.

EXAMPLE 19

N-Benzyloxycarbonylglycine (3.135 g., 0.015 mole) was dissolved in dry pyridine (30 ml.) and the solution was protected from atmospheric moisture (drying tube)) and stirred at −20° (acetone-solid CO$_2$ bath). Benzenesulphonyl chloride (1.94 g., 1.41 ml., 0.011 mole) was added over 5 min. Stirring at −20° was continued for 10 min. A solution of aphidicolin (3.38 g., 0.01 mole) in pyridine (30 ml.) at −20° was added. The mixture was stirred for 70 min. and then poured into water (500 ml.). The mixture was extracted with ethyl acetate (3×100 ml.) and the combined organic extracts were washed successively with N-hydrochloric acid (4×100 ml.), saturated sodium bicarbonate solution (100 ml.) and water (2×100 ml.). The organic phase was dried ($Na_2SO_4$) and the solvent evaporated in vacuo. The residual yellow oil was triturated with ethyl acetate (25 ml.), and the solid which crystallised was separated by filtration. The solid was crystallised twice from ethyl acetate to give 17-[N-benzyloxycarbonyl-glycyloxy)-3α,16β,18-trihydroxyaphidicolane, m.p. 179°–181°.

EXAMPLE 20

N-t-Butoxycarbonylglycine (0.75 g., 0.00429 mole) was dissolved in dry pyridine (5 ml.) and the solution was protected from atmospheric moisture (drying tube) and stirred. at −10° (ice-salt bath). Benzenesulphonyl chloride (0.554 g., 0.4 ml., 0.00314 mole) was added over 5 min. Stirring at −10° was continued for 10 min. and a solution of aphidicolin (1.0 g., 0.00301 mole) in dry pyridine (6 ml.) at −20° was then added. Stirring at −10° was continued for 1 hr. and the mixture was then poured into water (150 ml.) and extracted with ethyl acetate (3×75 ml.). The combined extracts were washed successively with 1.5N-hydrochloric acid (3×50 ml.), saturated sodium bicarbonate solution (3×25 ml.) and water (25 ml.). The organic solution was dried ($Na_2SO_4$) and the solvent evaporated in vacuo. The residue was crystallised from ethyl acetate to give 17-(N-t-butoxycarbonylglycyloxy)-3α,16β,18-trihydroxyaphidicolane, m.p. 193°–4°. A small sample was recrystallised from ethyl acetate:methanol 9:1 v/v; the crystals softened at 193°–4° and melted at 194°–6°.

EXAMPLE 21

17-(N-Benzyloxycarbonylglycyloxy)-3α,16β,18-trihydroxyaphidicolane (2.5 g., 0.00479 mole) was dissolved in dry ethanol (150 ml.) and the solution was added to a pre-hydrogenated suspension of 30% w/w palladium-on-charcoal catalyst (0.25 g.) in dry ethanol (150 ml.). The mixture was hydrogenated at ambient temperature and atmospheric pressure until no further hydrogen was consumed (approx. 100 ml. total; approx. 2.5 hr). The catalyst was removed by filtration (Celite; Trade Mark) and the solvent evaporated in vacuo from the filtrate. The residue was dissolved in ethanol (50 ml.), water (100 ml.) was added, and the solution was adjusted to pH 6 with 0.1N-hydrochloric acid. The ethanol was evaporated in vacuo (1 mm. pressure; solid $CO_2$ cold finger condenser) and the resulting aqueous solution was washed with ethyl acetate (4×50 ml.). The aqueous phase was evaporated in vacuo (1 mm. pressure; solid $CO_2$ cold finger condenser) to a volume of approx. 50 ml. and then freeze-dried. There was thus obtained 17-glycyloxy-3α, 16β, 18-trihydroxyaphidicolane hydrochloride as a white solid, NMR ($d_5$ pyridine solution, 90 MHz) : 2.71τ(ca. 10H, broad s, exchanged with $D_2O$), 5.43τ(2H,s) 5.60τ(2H,s), 6.05τ(1H, broad s), 6.11–6.50τ(2H, AB quartet, J=11.7 Hz), 9.01τ(3H, s) and 9.21τ(3H,s).

EXAMPLE 22

Aphidicolin (6.76 g., 0.02 mole) was dissolved in dry pyridine (100 ml.), and the solution was stirred at ambient temperature and protected from atmospheric moisture (drying tube). m-Chlorosulphonylbenzoic acid (8.82 g., 0.04 mole) was added to the stirred solution over 1 hr. The mixture was stirred for a further 3 hr. and the solvent then evaporated in vacuo (1 mm. pressure; solid $CO_2$ cold finger condenser). The residue was shaken together with ethyl acetate (300 ml.) and water (300 ml.), and the mixture was separated, both phases being retained. The aqueous phase was extracted with ethyl acetate (2×300 ml.). The combined organic phases were dried ($Na_2SO_4$) and the solvent evaporated in vacuo. The residue was chromatographed on silica gel (Merck Art. 9385, 200 g. ), eluting with ethyl acetate:-methanol 9:1 v/v and collecting 29 ml. fractions, to remove less polar impurities, and then with ethyl acetate: methanol:acetic acid 90:10:1 v/v. Fractions containing the desired product (detected by tlc) were combined and the solvent evaporated in vacuo. The residue was twice dissolved in a small volume of toluene and the solvent evaporated in vacuo.

The residues from the reactions carried out as described above were combined and chromatographed on silica gel (Merck Art. 9385, 100 g.), eluting with ethyl acetate:methanol:acetic acid 90:10:1 v/v and collecting 20 ml. fractions. Fractions 11 to 16 were combined, the solvents were evaporated in vacuo, and the residue was dissolved three times in a small volume of toluene and the solvent evaporated in vacuo. There was thus obtained 17-m-carboxybenzenesulphonyloxy-3α,16β,18-trihydroxyaphidicolane as a white solid, NMR ($CDCl_3$-dimethyl sulphoxide solution, 90 MHz) : 1.54τ(1H, broad s), 1.76τ(1H, d, J=7.2 Hz), 2.00τ(1H, d, J=7.2 Hz), 2.40τ (1H, t, J=7.2 Hz), 6.18τ (1H,s), 6.47τ(1H, broad s), 6.50–6.87τ(2H, AB quartet, J=11.7 Hz), 9.10τ(3H, s) and 9.37τ (3H, s).

The sodium salt was prepared by dissolving the free acid (0.20 g.) in a mixture of methanol (25 ml.) and water (35 ml.) and adjusting the solution at 0° to pH 7.5 with 0.1N-sodium hydroxide. The resulting solution was evaporated in vacuo (0.1 mm; solid $CO_2$ cold finger condenser) to a volume of approx. 25 ml. and then freeze-dried to give the sodium salt as a white voluminous solid.

EXAMPLE 23

Aphidicolin (3.38 g., 0.01 mole) was dissolved in dry pyridine (50 ml.) and the solution was stirred at ambient temperature and protected from atmospheric moisture (drying tube). 1-Dimethylaminonaphthalene-5-sulphonyl chloride (4.04 g., 0.015 mole) was added to the stirred solution over 2 hr. Stirring was continued for a further hour and the solvent was then evaporated in vacuo (1 mm. pressure; solid $CO_2$ cold finger condenser). The residue was shaken together with ethyl acetate (60 ml.) and water (70 ml.) and the mixture was separated, both phases being retained. The aqueous phase was extracted with ethyl acetate (20 ml.) and the combined organic phases were dried ($Na_2SO_4$) and the solvent evaporated in vacuo. The residual pale yellow solid was chromatographed on silica gel (Merck Art. 9385, 350 g.), eluting with ethyl acetate and collecting 32 ml. fractions. Fractions 10 to 24 were combined and the solvent evaporated in vacuo to give 17-(1-dimethylaminonaphthalene-β-sulphonyloxy)-3α,16β,15-trihydroxyaphidicolane as a pale yellow solid which showed no clear melting point and which decomposed above 255°. The product had NMR ($d_6$ dimethyl sulphoxide solution plus $d_4$ acetic acid, 90 MHz): 1.38τ(1H, d, J=7.5Hz), 1.77τ(2H, m), 2.33τ (2H, t, J=7.5Hz), 1.72τ(1H, d, J=7.5Hz), 6.28 τ(2H, s), 6.55τ(1H, broad s), 6.57–7.0τ(2H, AB quartet, J=12Hz), 7.1τ(6H, s), 9.13τ(3H, s) and 9.37τ(3H, s).

What we claim is:

1. A compound of the formula:

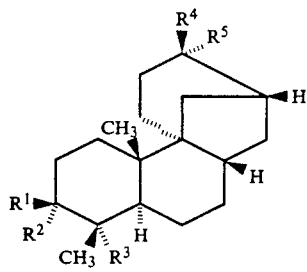

wherein:
R¹ is hydrogen;
R² is a hydroxy radical;
R³ is a hydroxmethyl radical
R⁴ is a hydroxy radical;
R⁵ is a formyl radical, a radical of the formula -CHR⁷OH, wherein R⁷ is an alkyl radical of not more than 3 carbon atoms, or R⁵ is a group of the formula -CH₂O.CO.OR⁸, wherein R⁸ is a phenyl radical or a phenylalkyl radical of not more than 9 carbon atoms, or R⁸ is an N-substituted piperidinyl radical of the formula:
wherein R⁶ is a phenylalkyl radical of not more than 9 carbon atoms, or R⁴ and R⁵ are joined together to form the group —O.CO.OCH₂—, provided that when R⁵ is a radical of the formula —CH(CH₃)OH and a pair of diastereoisomers is obtained then the less polar diastereoisomer is excluded.

2. The compound as claimed in claim 1 wherein R³ is a hydroxymethyl radical;
R⁴ is a hydroxy radical;
R⁵ is a formyl radical or a radical of the formula —CHR⁷OH, wherein
R⁷ is an alkyl radical of not more than 3 carbon atoms, or R⁵ is a group of the formula -CH₂O.CO.OR⁸, wherein R⁸ is a phenyl radical; or R⁴ and R⁵ are joined together to form the group —O.CO.OCH₂—, provided that when R⁵ is a radical of the formula -CH(CH₃)OH and a pair of diastereoisomers is obtained then the less polar diastereoisomer is excluded.

3. The compound as claimed in claim 2 wherein R⁵ is a formyl radical or a radical of the formula —CH(CH₃)OH, provided that when R⁵ is a radical of the formulas -CH(CH₃)OH and a pair of diastereoisomers is obtained then the less polar diastereoisomer is excluded.

4. The more polar diastereoisomer of the compound as claimed in claim 2 wherein R⁵ is a radical of the formula —CH(CH₃)OH.

5. The more polar isomer of the pair of diastereoisomers of 3α,16β, 17, 18-tetrahydroxy-17-methylaphidicolane.

6. A pharmaceutical composition for inhibiting the activity of DNA-containing viruses comprising an effective amount of a compound of the formula II as defined in claim 1 or claim 5 and a pharmaceutically-acceptable diluent or carrier.

7. A method of inhibiting the activity of a DNA-containing virus which comprises contacting said virus with a compound of formula II as defined in claim 1 or claim 5 under conditions such that the activity of said virus is inhibited.

* * * * *